US007252826B2

(12) United States Patent
Hsu et al.

(10) Patent No.: US 7,252,826 B2
(45) Date of Patent: Aug. 7, 2007

(54) MODIFIED MITE ALLERGEN AND PHARMACEUTICAL USES THEREOF

(75) Inventors: Ching-Hsiang Hsu, Tainan County (TW); Wei-Chih Su, Tainan County (TW)

(73) Assignee: GenMont Biotech Inc. (TW)

( * ) Notice: Subject to any disclaimer, the term of this patent is extended or adjusted under 35 U.S.C. 154(b) by 370 days.

(21) Appl. No.: 10/654,020

(22) Filed: Sep. 4, 2003

(65) Prior Publication Data

US 2004/0091499 A1 May 13, 2004

Related U.S. Application Data

(60) Provisional application No. 60/424,310, filed on Nov. 7, 2002.

(51) Int. Cl.
*A61K 39/00* (2006.01)

(52) U.S. Cl. ................................ 424/185.1; 424/139.1; 530/350; 530/868

(58) Field of Classification Search ..................... None
See application file for complete search history.

(56) References Cited

U.S. PATENT DOCUMENTS 6,187,311 B1 2/2001 Nishiyama et al.

OTHER PUBLICATIONS

Blumenthal et al. In Allergens and Immunotherapy, third edition, Marcel Dekker, Inc., 2004, pp. 37-50.*
Burks et al., Eur J Biochem, 1997, 245:334-339.*
Reese et al., J Immunol, 2005, 175:8354-8364.*
Niu et al., Respiratory Medicine, Epub on Jan. 3, 2006, 10 pages.*
Merriam-Webster OnLine Dictionary entry for prevent, downloaded Apr. 26, 2006, 2 pages.*
Lin et al., "Allergens, IgE, mediators, inflammatory mechanisms—Characterization of Der p V allergen, cDNA analysis, and IgE-mediated reactivity to the recombinant protein", *J. Allergy Clin Immunol*, Dec. 1994, pp. 989-996, vol. 94, No. 8, Part 1.
van Hage-Hamsten et al., "Mechanisms of allergy—Skin test evaluation of genetically engineered hypoallergenic derivatives of the major birch pollen allergen, Bet v 1: Results obtained with a mix of two recombinant Bet v 1 fragments and recombinant Bet v 1 trimer in a Swedish population before the birch pollen season", *J. Allergy Clin Immunol*, Nov. 1999, pp. 969-977, vol. 104, No. 5.
Beezhold et al., "Mutational analysis of the IgE epitopes in the latex allergen Hev b 5", *J. Allergy Clin Immunol*, Jun. 2001, pp. 1069-1076, vol. 107, No. 6.
QuikChange Site-Directed Mutagenesis Kit. Instruction Manual. Catalog #200518 (30 reactions) and #200519 (10 reactions). Revision #0582008g.
Cell Proliferation ELISA, BrdU (colorimetric). Colorimetric immunoassay for the quantification of cell proliferation, based on the measurement of BrdU incorporation during DNA synthesis: A non-radioactive alternative to the [$^3$H]-thymidine incorporation assay. Cat. No. 1647229, 1 kit [1000 tests]. Instruction Manual. Version 4, Dec. 2001.

* cited by examiner

*Primary Examiner*—G. R. Ewoldt
*Assistant Examiner*—Michael Szperka
(74) *Attorney, Agent, or Firm*—Banner & Witcoff, Ltd.

(57) ABSTRACT

The present invention provides a modified *Dermatophagoides pteronyssinus* allergen Der p 5 protein which has ability to inhibit IgE binding when exposed against to the antigen. A method for treating allergy comprising administrating a therapeutically effective dose of the modified *D. pteronyssinus* allergen Der p 5 protein to a subject suffering from allergy Der p 5 is also provided.

8 Claims, 6 Drawing Sheets

MODIFIED MITE ALLERGEN AND PHARMACEUTICAL USES THEREOF

This application claims the benefit of provisional application Ser. No. 60/424,310 filed Nov. 7, 2002, the contents of which are expressly incorporated herein.

BACKGROUND OF THE INVENTION

1. Field of the Invention

The invention mainly relates to a modified allergen obtained by altering Der p 5 allergen of house dust mite and the pharmaceutical uses thereof.

2. Description of the Related Art

Allergy refers to an acquired potential to develop immunologically mediated adverse reaction to normally innocuous substances. Allergic reaction provokes symptoms such as itching, coughing, wheezing, sneezing, watery eyes, inflammation and fatigue. Many allergic diseases are due to several kinds of symptoms which are developed by sensitization to the antigen causing the diseases. In an allergic disease, an IgE antibody specific for an allergen (e.g. pollens and mite dust) in blood serum and tissue is produced, and when the antibody is exposed again to the antigen, the antibody reacts with the antigen in each tissue. It is normally believed that an allergic reaction includes an early specific immune response and a late inflammatory reaction. It is reported that an allergen mediates the early phase of allergy by stimulating high affinity immunoglobulin (IgE) receptors. Mast cells and basophils, when stimulated by allergens, will release histamine and cytokines. The cytokines released from mast cells and basophils then mediate the late phase of allergy by recruiting inflammatory cells.

It is reported that allergic diseases, such as bronchial asthma, childhood asthma, atopic dermatitis and the like, are mainly caused by allergens from mites living in house dust. Several kinds of proteins of mite allergens, such as Der p 1 and Der p 2, have been identified. Der p 5 is a 14-k Da group 5 mite allergen which contains a 19-residue leader protein and a 113-residue mature protein was cloned and sequenced (Lin et al., Allergens, IgE, mediators, inflammatory mechanisms. *J Allergy Clin Immunol* 1994; 6:989-996). Although only 60% of mite-allergic children reacted to Der p 5, the IgE reactivity appeared to be stronger than that of Der p 1 and Der p 2 in Taiwan. Furthermore, among the various allergic diseases, the group of children with asthma have significant more reactivity than the group with rhinitis alone. Der p 5 is regarded as a clinically significant allergen in mite allergy.

Various therapies have been pursued in order to treat the symptoms of allergies. Particularly, "oral tolerance" is considered to be an ideal candidate for treatment of an allergic disease. Oral tolerance has been characterized as a state of antigen-specific systemic immunological unresponsiveness or tolerance, which is induced by prior oral administration or feeding of antigen. The primary mechanism by which an orally administered antigen induces tolerance is believed to be via the generation of active suppression or clonal anergy.

However, directly administrating wild-type mite allergens may raise an allergic reaction, namely anaphylactic shock, in hyposensitization therapy, because the activity of these wild-type allergens is high. If the binding between the antigen and the IgE antibody is controlled, the crosslinking among the IgE antibodies on mast cells or basophils, and the release of histamine and cytokines are controlled to treat allergic diseases. Regarding Der p 1 and Der p 2, the B-cell epitopes and T-cell epitopes have been demonstrated, and the side-directed mutagenesis of Der p 1 and Der p 2 in order to inhibit IgE binding when exposed again to the antigen has been disclosed in U.S. Pat. No. 6,187,311, but nothing on Der p 5 has been disclosed.

SUMMARY OF THE INVENTION

The invention provides a modified *Dermatophagoides pteronyssinus* allergen Der p 5 protein, which provides an efficacy in inhibiting IgE binding when exposed again to the antigen in a subject or has a lower allergen activity than wide-type allergens. Therefore, the invention provides a method for treating an allergic disease using the modified *D. pteronyssinus* allergen Der p 5 protein, in which no anaphylactic shock shows.

One subject of the invention is to provide a modified *Dermatophagoides pteronyssinus* allergen Der p 5 protein comprising some substitutions at one or more residue positions corresponding to the 44$^{th}$, 77$^{th}$, 99$^{th}$, and 103$^{rd}$ amino acid residues of the wild-type *D. pteronyssinus* allergen Der p 5 protein, in order to minimize the structural change and provide an efficacy in inhibiting IgE binding when exposed again to the antigen in a subject and reducing in vivo allergic reactivity but retaining the ability to trigger peripheral blood mononuclear cell (PBMC) proliferation. The modified mite allergen Der p 5 protein according to the invention can inhibit IgE binding when exposed again to the antigen.

Another object of the invention is to provide an isolated nucleic acid molecule having a nucleotide sequence encoding the modified *pteronyssinus* allergen Der p 5 protein according to the invention. In one embodiment of the invention, the isolated DNA molecule comprises one or more substitutions of the nucleotide sequence of SEQ ID NO:1.

In another aspect, the invention provides a host cell comprising the isolated nucleic acid molecule.

The present invention involves a pharmaceutical composition for treating allergic diseases in association with Der p 5 or immunizing against allergic diseases in association with Der p 5, comprising a therapeutically effective dose of the modified *D. pteronyssinus* allergen Der p 5 protein according to the invention and a pharmaceutically acceptable carrier.

The present invention also involves a method for treating allergic diseases in association with Der p 5 which comprises administrating a therapeutically effective dose of the modified *D. pteronyssinus* allergen Der p 5 protein according to the invention to a subject suffering from allergic diseases, particularly in association with Der p 5.

DETAILED DESCRIPTION OF THE INVENTION

Figure 1:
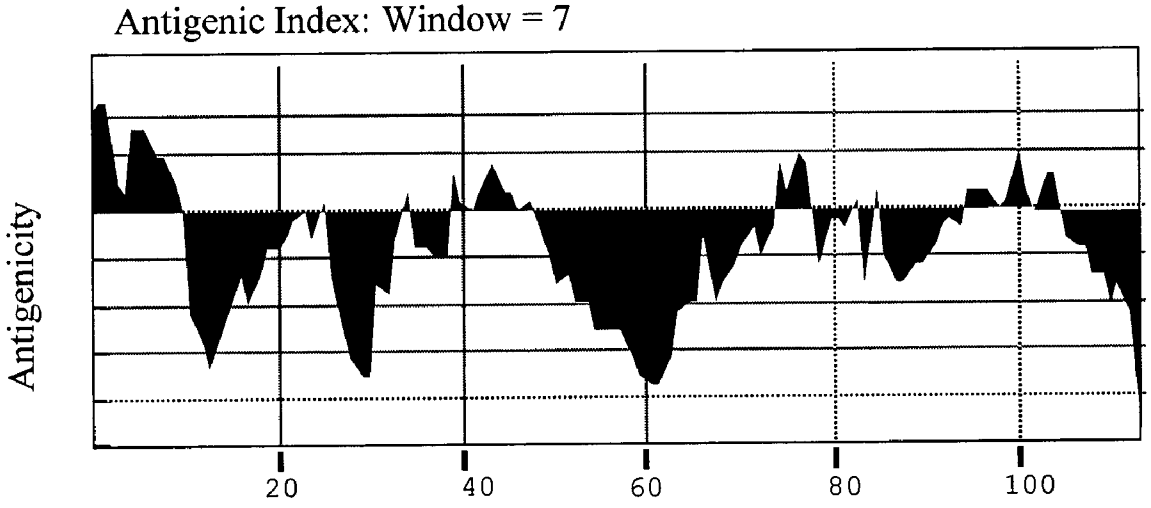
FIG. 1 illustrates the result of the wild-type Der p 5 antigenicity simulation.

The aim of the invention is to produce a hypoallergenic form of Der p 5.

The invention provides a modified *Dermatophagoides pteronyssinus* allergen Der p 5 protein, which provides an efficacy in inhibiting IgB binding when exposed again to the antigen in a subject or has a lower allergen activity than wild-type allergens. In one embodiment of the invention, the wild-type allergen has the amino acid sequence of SEQ ID NO:2. According to the invention, the substitutions are at one or more residue positions corresponding to the $44^{th}$, $77^{th}$, $99^{th}$, and $103^{rd}$ amino acid residues of the wild-type mite allergen Der p 5 protein.

The term "modified *Dermatophagoides pteronyssinus* allergen" used herein refers to a gene-engineered mite allergen of which the amino acid sequence is different from that of wild-type allergen. The modified allergen of the present invention can be produced by any method suitable to the aims of the present invention, and preferably by a site-directed mutagenesis method, and more preferably a PCR method. For example, the $44^{th}$ proline residue of the modified Der p 5 protein (SEQ ID NO:4) is replaced with an alanine residue using the DNA chain as shown in SEQ ID NO:3.

In a preferred embodiment of the invention, sites to be modified of the mite allergen (Der p 5) are estimated both in antigenicity and hydrophilicity. The term "antigenicity" used herein refers to ability or a tendency to elicit an allergic response. The antigenicity usually relates to IgE binding ability, B cell binding ability, T cell binding ability, and peripheral blood mononuclear cell (PBMC) proliferation stimulating ability. Epitopes of antigen play a crucial role in antigenicity, and the three-dimensional configuration and hydrophilicity are also important. It is acceptable to decrease the antigenicity by changing the configuration of the epitopes but retaining the same hydrophilicity and structure of the total allergen. Many commercial computer software packages are well established for simulating the theoretical antigenicity of an antigen such as MacVector 6.05 computer model.

Several amino acid residues of Der p 5 are shown to dominate the antigenicity, which comprise the aspartic acid at the $2^{nd}$ position, the aspartic acid at the $6^{th}$ position, the glutamine at the $8^{th}$ position, the proline at the $44^{th}$ position, the lysine at the $77^{th}$ position, the arginine at the $99^{th}$ position, and the lysine at the $103^{rd}$ position, wherein preferably the sites are selected from the group consisting of the $44^{th}$, $77^{th}$, $99^{th}$, and $103^{rd}$ positions. According to the invention, the modified and hypoallergenic forms of Der p 5 are obtained by changing at least one the amino acid residue at these positions in the wild-type mite allergen Der p 5. In a more preferred embodiment, the modified mite allergen Der p 5 has a changed site at the $44^{th}$ position that is proline in the wild type.

Amino acid residues selected to replace the residues have different functional group in side chain from those in the wild-type Der p 5. In one embodiment of the invention, at least one of the residue of the wild type is substituted by an amino acid with an alkyl side chain, and in a preferred embodiment of the invention, the residue is substituted by alanine.

According to the invention, an isolated nucleic acid molecule having a nucleotide sequence encoding the modified *Dermatophagoides pteronyssinus* allergen Der p 5 protein according to the invention is also provided for manipulations, expression and storage. The isolated DNA molecule can be expressed by using a suitable vector, which can be expressed in a host cell. The term "host cell" used herein refers to a prokaryotic or eukaryotic cell which is transformed or transfected with the vector comprising the desired genes, wherein preferably, the host cell can express the desired genes to producing the gene products.

A method of producing the modified *Dermatophagoides pteronyssinus* allergen Der p 5 protein according to the invention is provided, which comprises culturing the host cell carrying the isolated nucleic acid molecule according to the invention under conditions such that said modified *Dermatophagoides pteronyssinus* allergen Der p 5 protein is expressed and produced thereby, and isolating said modified *Dermatophagoides pteronyssinus* allergen Der p 5 protein.

According to the invention, the modified *Dermatophagoides pteronyssinus* allergen Der p 5 protein changed in antigenicity can be used in treating Der p 5 allergic disease which comprises administrating a therapeutically effective dose of the modified *Dermatophagoides pteronyssinus* allergen Der p 5 to a subject suffering from Der p 5 allergic disease. Because the antigenicity of the modified mite allergen is reduced, anaphylactic shock which may be raised in directly administrating wild-type mite allergens in hyposensitization therapy is avoided. The binding between the antigen and the IgE antibody is controlled and the cross-linking among the IgE antibodies on mast cells or basophils, and the release of chemical mediators are controlled to treat allergic diseases. However, the ability to stimulate PBMC proliferation is still retained.

The term "allergic disease" used herein refers to allergy in association with Der p 5. The allergic disease includes rhinitis, sinusitis, asthma, hypersensitive pneumonia, extrinsic allergic alveolitis, conjunctivitis, urticaria, eczema, dermatitis, anaphylaxis, angioedema, allergic and migraine headache, and certain gastrointestinal disorders.

The following Examples are given for the purpose of illustration only and are not intended to limit the scope of the present invention.

EXAMPLE 1

Modified Mite Allergen Der p 5 Construction

Antigenicity of Der p 5 simulation. The theoretical IgE epitopes of Der p 5 were predicted with MacVector 6.05 computer model. The amino acid sequence of wild-type Der p 5 was input and calculated according to Antigenic Index listed below (according to MacVector operating guide):

$$\text{Antigenic Index}=\Sigma\{0.3\ \text{hydro}[i]+0.15\text{surf\_prob}[i]+0.15\ \text{flex}[i]+0.2\ \text{chou\_fas}[i]+0.2\text{rob\_garn}[i]\}$$

Figure 2:
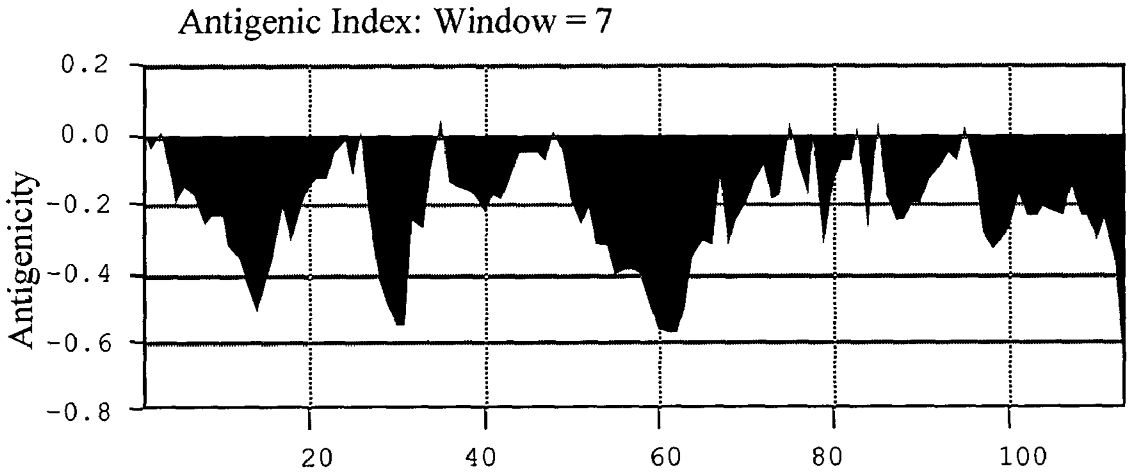
FIG. 2 illustrates the result of the wild-type Der p 5 with several substitutions, in which the antigenicity simulation was changed.

The antigenicity of wild-type Der p 5 simulated was shown in FIG. 1. Several sites regarded as having high antigenicity comprising $D^2$, $D^6$, $Q^8$, $p^{44}$, $K^{77}$, $R^{99}$, and $K^{103}$ were replaced with alanine residue and then input the new amino acid sequence for simulation. The result was shown in FIG. 2. According to the simulation result, the Der p 5 with these sites changed had low antigenicity. For the reason, mutations at these sites were candidates for constructing the hypoallergenic form of Der p 5.

Site-directed mutagenesis: Wild-type Der p 5 gene (SEQ ID NO:1) was cloned in a pQE 60 vector and then mutated by using the QuickChange Site-Directed Mutagenesis Kit (Stratagene). The method for constructing the modified Der p 5 was described in the instruction manual of the kit. Dp5p-m2 (Der p 5 with the proline residue at position 44 replaced with alanine) were constructed by using DP5-2F 5'-CATTTTGAAGAAAAAGCGACAAAA-GAAATGAAAG-3' (SEQ ID NO:9) and DP5-2R 5'-CTTTCATTTCTTTTGTCGCTTTTTCTTCAAAATG-3' (SEQ ID NO:10). The codon CCG was changed to GCG and the proline was changed to alanine. Dp5p-m3 (Der p 5 with the lysine residue at position 77 replaced with alanine) were constructed by using DP5-3F 5'-GATCGTCTTATG-CAACGTGCAGATTTAGATA-3' (SEQ ID NO:11) and DP5-3R 5'-TATCTAAATCTGCACGTTGCATAAGAC-GAT-3' (SEQ ID NO:12). The codon AAA was changed to GCA and the lysine was changed to alanine. Dp5p-m4 (Der p 5 with the arginine residue at position 99 and the lysine residue at position 103 replaced with alanine) were constructed by using DP5-4F 5'-CATCACGGATC-CGAAGCTAAAAAACATGATTATGCGAAT-3' (SEQ ID NO:13) and DP5-4R 5'-CGCGCAAGCTTTTAAACT-TCAATCTTTTTAACACGTGCTTCTTCT GCTTTCAAATCAGCTTC-3' (SEQ ID NO:14). The codon usage CGT is changed to GCT and AAA is changed to GCA, and thus the arginine and lysine are both changed to alanine.

Figure 3:
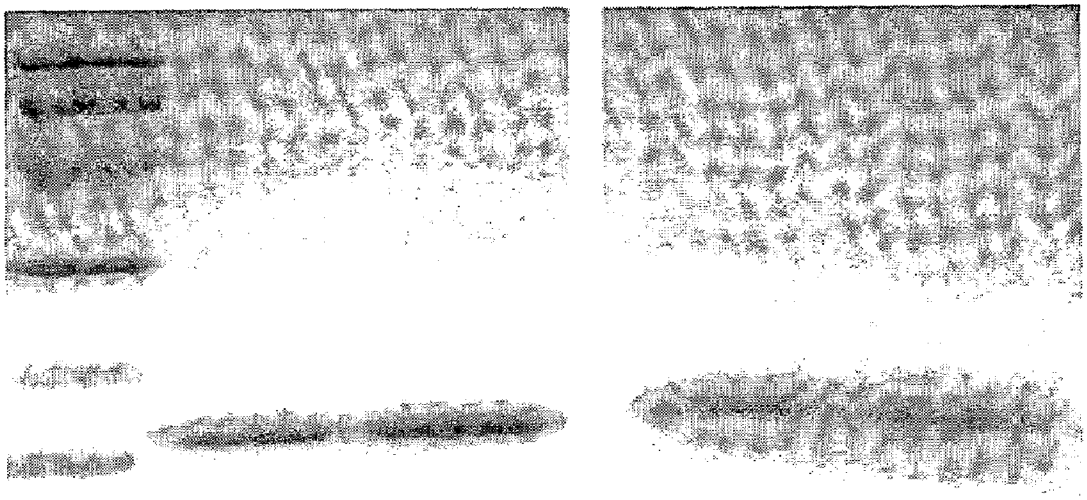
FIG. 3 illustrates the electrophoresis results of the wild type and modified Der p 5 resolved on an SDS-polyacrylamide gel.

Protein expression: The plasmids containing Der p 5, Dp5p-m2, Dp5p-m3, and Dp5p-m4 were transformed into *Escherichia coli* (M15) XL1-Blue for expression. The bacteria were cultured and the proteins expressed were subjected to sodium dodecyl sulfate polyacrylamide gel electrophoresis (SDS-PAGE). The protein sizes of the modified allergen and that of the wild-type Der p 5 were the same (about 14 k Da). The result show that the side-directed mutagenesis was successfully performed (referring to FIG. 3).

EXAMPLE 2

IgE Binding Inhibition of The Modified Mite Allergens

The method for assaying IgE binding inhibition of the modified mite allergens was based on the description by Beezhold et al. (Beezhold et al., Mutational analysis of the IgE epitopes in the latex allergen Hev b 5. *J Allergy Clin Immunol* 2001; 107:1069-1076). Sera from six mite allergy patients who were highly reactive to Der p 5 were taken for the assay. Standardized wild type mite allergen Der p 5 were coated on an ELISA plate, and then blocked. The sera were mixed with the wild-type and modified mite allergens (as inhibitors) and then reacted with Der p 5 coated on the ELISA plate. Biotin-labeled anti-human IgE was then added. Streptavidin-Alkaline phosphatase (Streptavidin-AKP) was labeled and p-Nitrophenyl phosphate (pNpp) was then added as substrate. The absorbance at 405 nm was measured. The percentage inhibition was calculated as below:

$$[1-(OD \text{ of Inhibitor}-OD \text{ of Background})/(OD \text{ of Non-Inhibition}-OD \text{ of Background})]\times 100\%$$

Figure 4:
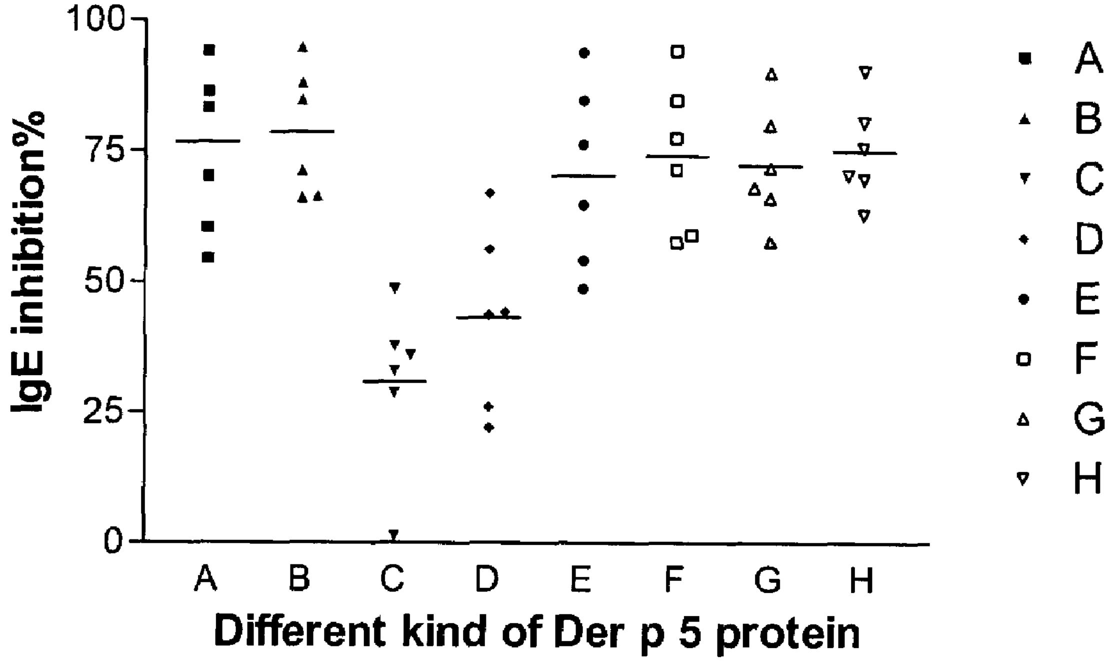
FIG. 4 illustrates the result of IgE inhibition ELISA, wherein A presents 10 μg Der p 5; B presents 50 μg Der p 5; C presents 10 μg Dp5p-m2; D presents 50 μg Dp5p-m2; E presents 10 μg Dp5p-m3; F presents 50 μg Dp5p-m3; G presents 10 μg Dp5p-m4; and H presents 50 μg Dp5p-m4.

The result of IgE inhibition ELISA was shown in FIG. 4. Comparing the wild type and the modified allergens, Dp5p-m2 had stronger ability to inhibit IgE binding when exposed again to the antigen.

EXAMPLE 3

Intradermal Skin Test

The method for assaying intradermal skin test was similar with the description by van Hage-Hamsten et al. (van Hage-Hamsten et al., Skin test evaluation of genetically engineered hypoallergenic derivatives of the major birch pollen allergen, Bet v 1: Results obtained with a mix of two recombinant Bet v 1 fragments and recombinant Bet v 1 trimer in a Swedish population before the birch pollen season. *J Allergy Clin Immunol* 1999; 104:969-977). Eight Der p 5 sensitive mite allergy patients were chosen. The wild type and modified Der p 5 were diluted to 1 mg/mL, and 0.05 mL of allergens was taken for each injection site on the patients' forearms 5 cm apart. A reaction of greater than 5×5 mm (diameter) for 15 min. after injection was regarded as a positive response.

Figure 5:
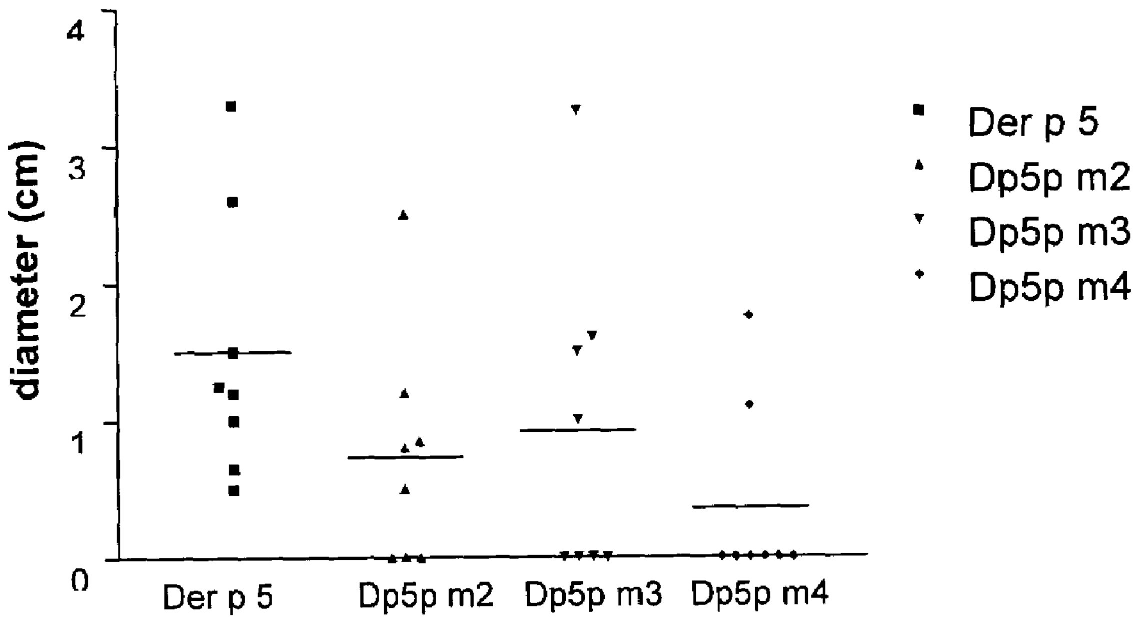
FIG. 5 illustrates the result of intradermal skin test.

The result of intradermal skin test was shown in FIG. 5. All of the modified Der p 5 had lower allergic response than the wild type in the intradermal skin test.

EXAMPLE 4

PBMC Proliferation Assay

The PBMC proliferation assay was performed by using Cell Proliferation ELISA, BrdU (calorimetric) kit (Roche), and the method was described in the instruction manual of the kit. PBMCs at various concentrations (from Der p 5 sensitive mite allergy Patient 1 and Patient 2) were cultured with wild-type and modified Der p 5 for 2 days. PBMCs cultured with Phaseolus vulgaris agglutinin (PHA) were as the positive control and PBMCs cultured only were as the negative control. The cells were pulsed with BrdU and harvested overnight, and then anti-BrdU-peroxidase (POD) was added. Tetramethyl-benzidine (TMB) as substrate was added and the spectrum of mixture was measure at 655 nm.

Figure 6A:
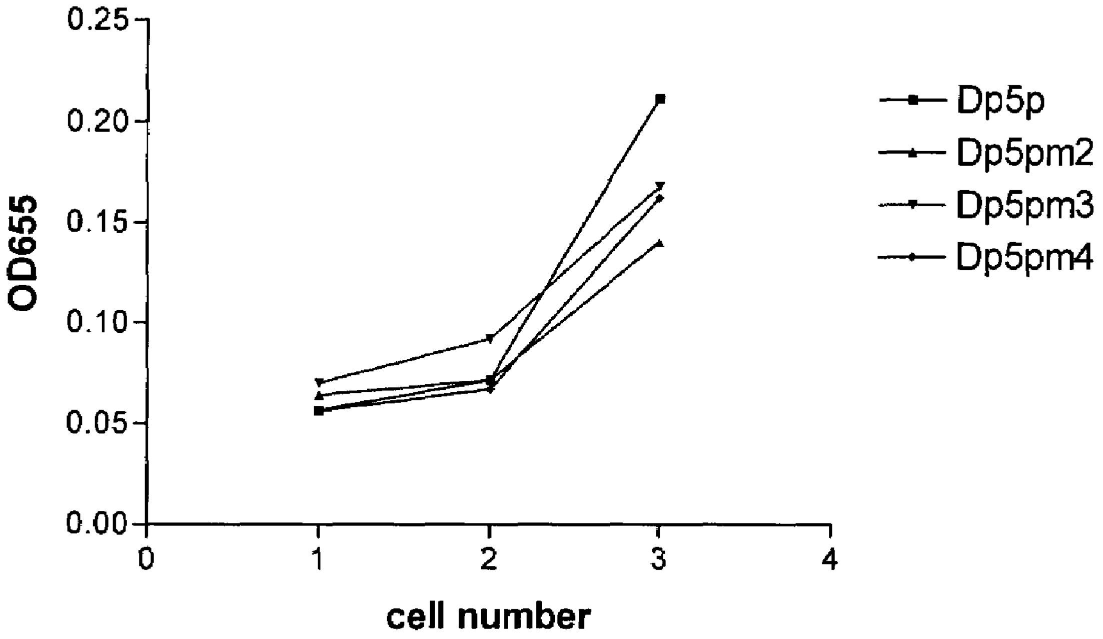
FIGS. 6*a* and 6*b* illustrate the result of PBMC proliferation assay of Patient 1 and Patient 2, respectively.
Figure 6B:
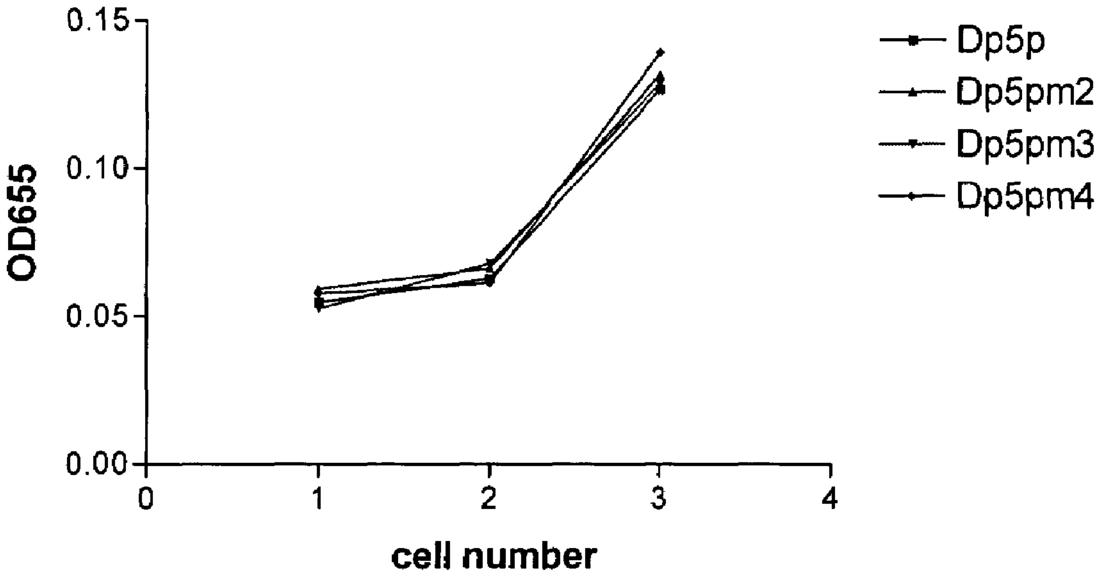

The results of the PBMC proliferation assay were shown in FIG. 6*a* (Patient 1) and FIG. 6*b* (Patient 2). The numbers of PBMC cultured with wild-type and modified Der p 5 were similar. It was shown that the stimulating PBMC proliferation ability of the modified Der p 5 was retained.

While embodiments of the present invention have been illustrated and described, various modifications and improvements can be made by persons skilled in the art. It is intended that the present invention is not limited to the particular forms as illustrated, and that all the modifications not departing from the spirit and scope of the present invention are within the scope as defined in the appended claims.

What is claimed is:

1. A modified *Dermatophagoides pteronyssinus* allergen Der p 5 protein, wherein at least one of amino acid residues 44, 77, 99, and 103 of wild-type *D. pteronyssinus* allergen Der p 5 protein of SEQ ID NO.2 is substituted with alanine.

2. The modified *D. pteronyssinus* allergen Der p 5 protein according to claim 1, wherein the modified *D. pteronyssinus* allergen Der p 5 protein has the amino acid sequence selected from the group consisting of the sequences of SEQ ID NOs:4, 6 and 8.

3. A pharmaceutical composition comprising a therapeutically effective dose of the modified *D. pteronyssinus* allergen Der p 5 protein according to claim 1 and a pharmaceutically acceptable carrier.

4. A pharmaceutical composition comprising a therapeutically effective dose of the modified *D. pteronyssinus* allergen Der p 5 protein according to claim 2 and a pharmaceutically acceptable carrier.

5. The modified *D. pteronyssinus* allergen Der p 5 protein according to claim 1, wherein amino acid residue 44 of wild-type *D. pteronyssinus* allergen Der p 5 protein of SEQ ID NO: 2 is substituted with alanine.

6. The modified *D. pteronyssinus* allergen Der p 5 protein according to claim 1, wherein amino acid residue 77 of wild-type *D. pteronyssinus* allergen Der p 5 protein of SEQ ID NO: 2 is substituted with alanine.

7. The modified *D. pteronyssinus* allergen Der p 5 protein according to claim 1, wherein amino acid residue 99 of wild-type *D. pteronyssinus* allergen Der p 5 protein of SEQ ID NO: 2 is substituted with alanine.

8. The modified *D. pteronyssinus* allergen Der p 5 protein according to claim 1, wherein amino acid residue 103 of wild-type *D. pteronyssinus* allergen Der p 5 protein of SEQ ID NO: 2 is substituted with alanine.

* * * * *

SEQUENCE LISTING

```
<160> NUMBER OF SEQ ID NOS: 14

<210> SEQ ID NO 1
<211> LENGTH: 342
<212> TYPE: DNA
```

-continued

<213> ORGANISM: Dermatophagoides pteronyssinus
<220> FEATURE:
<221> NAME/KEY: CDS
<222> LOCATION: (1)..(339)

<400> SEQUENCE: 1 gaa gat aaa aaa cat gat tat caa aat gaa ttt gat ttc tta ttg atg 48
Glu Asp Lys Lys His Asp Tyr Gln Asn Glu Phe Asp Phe Leu Leu Met
1 5 10 15 gaa cgt att cat gaa caa att aaa aaa ggt gaa ctt gca ttg ttc tat 96
Glu Arg Ile His Glu Gln Ile Lys Lys Gly Glu Leu Ala Leu Phe Tyr
20 25 30 ctt caa gaa cag att aat cat ttt gaa gaa aaa ccg aca aaa gaa atg 144
Leu Gln Glu Gln Ile Asn His Phe Glu Glu Lys Pro Thr Lys Glu Met
35 40 45 aaa gat aaa att gta gcc gaa atg gat acc att att gct atg atc gat 192
Lys Asp Lys Ile Val Ala Glu Met Asp Thr Ile Ile Ala Met Ile Asp
50 55 60 ggt gta cgt ggt gta ctt gat cgt ctt atg caa cgt aaa gat tta gat 240
Gly Val Arg Gly Val Leu Asp Arg Leu Met Gln Arg Lys Asp Leu Asp
65 70 75 80 att ttt gaa caa tat aat ctt gaa atg gct aaa aaa tct ggt gat att 288
Ile Phe Glu Gln Tyr Asn Leu Glu Met Ala Lys Lys Ser Gly Asp Ile
85 90 95 ttg gaa cgt gat ttg aaa aaa gaa gaa gca cgt gtt aaa aag att gaa 336
Leu Glu Arg Asp Leu Lys Lys Glu Glu Ala Arg Val Lys Lys Ile Glu
100 105 110 gtt taa 342
Val

<210> SEQ ID NO 2
<211> LENGTH: 113
<212> TYPE: PRT
<213> ORGANISM: Dermatophagoides pteronyssinus

<400> SEQUENCE: 2

Glu Asp Lys Lys His Asp Tyr Gln Asn Glu Phe Asp Phe Leu Leu Met
1 5 10 15

Glu Arg Ile His Glu Gln Ile Lys Lys Gly Glu Leu Ala Leu Phe Tyr
20 25 30

Leu Gln Glu Gln Ile Asn His Phe Glu Glu Lys Pro Thr Lys Glu Met
35 40 45

Lys Asp Lys Ile Val Ala Glu Met Asp Thr Ile Ile Ala Met Ile Asp
50 55 60

Gly Val Arg Gly Val Leu Asp Arg Leu Met Gln Arg Lys Asp Leu Asp
65 70 75 80

Ile Phe Glu Gln Tyr Asn Leu Glu Met Ala Lys Lys Ser Gly Asp Ile
85 90 95

Leu Glu Arg Asp Leu Lys Lys Glu Glu Ala Arg Val Lys Lys Ile Glu
100 105 110

Val

<210> SEQ ID NO 3
<211> LENGTH: 342
<212> TYPE: DNA
<213> ORGANISM: Artificial
<220> FEATURE:
<223> OTHER INFORMATION: synthetic mutant
<220> FEATURE:
<221> NAME/KEY: CDS
<222> LOCATION: (1)..(339)

-continued

<400> SEQUENCE: 3

```
gaa gat aaa aaa cat gat tat caa aat gaa ttt gat ttc tta ttg atg       48
Glu Asp Lys Lys His Asp Tyr Gln Asn Glu Phe Asp Phe Leu Leu Met
1               5                   10                  15

gaa cgt att cat gaa caa att aaa aaa ggt gaa ctt gca ttg ttc tat       96
Glu Arg Ile His Glu Gln Ile Lys Lys Gly Glu Leu Ala Leu Phe Tyr
            20                  25                  30

ctt caa gaa cag att aat cat ttt gaa gaa aaa gcg aca aaa gaa atg      144
Leu Gln Glu Gln Ile Asn His Phe Glu Glu Lys Ala Thr Lys Glu Met
        35                  40                  45

aaa gat aaa att gta gcc gaa atg gat acc att att gct atg atc gat      192
Lys Asp Lys Ile Val Ala Glu Met Asp Thr Ile Ile Ala Met Ile Asp
    50                  55                  60

ggt gta cgt ggt gta ctt gat cgt ctt atg caa cgt aaa gat tta gat      240
Gly Val Arg Gly Val Leu Asp Arg Leu Met Gln Arg Lys Asp Leu Asp
65                  70                  75                  80

att ttt gaa caa tat aat ctt gaa atg gct aaa aaa tct ggt gat att      288
Ile Phe Glu Gln Tyr Asn Leu Glu Met Ala Lys Lys Ser Gly Asp Ile
                85                  90                  95

ttg gaa cgt gat ttg aaa aaa gaa gaa gca cgt gtt aaa aag att gaa      336
Leu Glu Arg Asp Leu Lys Lys Glu Glu Ala Arg Val Lys Lys Ile Glu
            100                 105                 110

gtt taa                                                              342
Val
```

<210> SEQ ID NO 4
<211> LENGTH: 113
<212> TYPE: PRT
<213> ORGANISM: Artificial
<220> FEATURE:
<223> OTHER INFORMATION: synthetic mutant

<400> SEQUENCE: 4

```
Glu Asp Lys Lys His Asp Tyr Gln Asn Glu Phe Asp Phe Leu Leu Met
1               5                   10                  15

Glu Arg Ile His Glu Gln Ile Lys Lys Gly Glu Leu Ala Leu Phe Tyr
            20                  25                  30

Leu Gln Glu Gln Ile Asn His Phe Glu Glu Lys Ala Thr Lys Glu Met
        35                  40                  45

Lys Asp Lys Ile Val Ala Glu Met Asp Thr Ile Ile Ala Met Ile Asp
    50                  55                  60

Gly Val Arg Gly Val Leu Asp Arg Leu Met Gln Arg Lys Asp Leu Asp
65                  70                  75                  80

Ile Phe Glu Gln Tyr Asn Leu Glu Met Ala Lys Lys Ser Gly Asp Ile
                85                  90                  95

Leu Glu Arg Asp Leu Lys Lys Glu Glu Ala Arg Val Lys Lys Ile Glu
            100                 105                 110

Val
```

<210> SEQ ID NO 5
<211> LENGTH: 342
<212> TYPE: DNA
<213> ORGANISM: Artificial
<220> FEATURE:
<223> OTHER INFORMATION: synthetic mutant
<220> FEATURE:
<221> NAME/KEY: CDS
<222> LOCATION: (1)..(339)

<400> SEQUENCE: 5

-continued

```
gaa gat aaa aaa cat gat tat caa aat gaa ttt gat ttc tta ttg atg       48
Glu Asp Lys Lys His Asp Tyr Gln Asn Glu Phe Asp Phe Leu Leu Met
1               5                   10                  15

gaa cgt att cat gaa caa att aaa aaa ggt gaa ctt gca ttg ttc tat       96
Glu Arg Ile His Glu Gln Ile Lys Lys Gly Glu Leu Ala Leu Phe Tyr
            20                  25                  30

ctt caa gaa cag att aat cat ttt gaa gaa aaa ccg aca aaa gaa atg      144
Leu Gln Glu Gln Ile Asn His Phe Glu Glu Lys Pro Thr Lys Glu Met
        35                  40                  45

aaa gat aaa att gta gcc gaa atg gat acc att att gct atg atc gat      192
Lys Asp Lys Ile Val Ala Glu Met Asp Thr Ile Ile Ala Met Ile Asp
    50                  55                  60

ggt gta cgt ggt gta ctt gat cgt ctt atg caa cgt gca gat tta gat      240
Gly Val Arg Gly Val Leu Asp Arg Leu Met Gln Arg Ala Asp Leu Asp
65                  70                  75                  80

att ttt gaa caa tat aat ctt gaa atg gct aaa aaa tct ggt gat att      288
Ile Phe Glu Gln Tyr Asn Leu Glu Met Ala Lys Lys Ser Gly Asp Ile
                85                  90                  95

ttg gaa cgt gat ttg aaa aaa gaa gaa gca cgt gtt aaa aag att gaa      336
Leu Glu Arg Asp Leu Lys Lys Glu Glu Ala Arg Val Lys Lys Ile Glu
            100                 105                 110

gtt taa                                                              342
Val


<210> SEQ ID NO 6
<211> LENGTH: 113
<212> TYPE: PRT
<213> ORGANISM: Artificial
<220> FEATURE:
<223> OTHER INFORMATION: synthetic mutant

<400> SEQUENCE: 6

Glu Asp Lys Lys His Asp Tyr Gln Asn Glu Phe Asp Phe Leu Leu Met
1               5                   10                  15

Glu Arg Ile His Glu Gln Ile Lys Lys Gly Glu Leu Ala Leu Phe Tyr
            20                  25                  30

Leu Gln Glu Gln Ile Asn His Phe Glu Glu Lys Pro Thr Lys Glu Met
        35                  40                  45

Lys Asp Lys Ile Val Ala Glu Met Asp Thr Ile Ile Ala Met Ile Asp
    50                  55                  60

Gly Val Arg Gly Val Leu Asp Arg Leu Met Gln Arg Ala Asp Leu Asp
65                  70                  75                  80

Ile Phe Glu Gln Tyr Asn Leu Glu Met Ala Lys Lys Ser Gly Asp Ile
                85                  90                  95

Leu Glu Arg Asp Leu Lys Lys Glu Glu Ala Arg Val Lys Lys Ile Glu
            100                 105                 110

Val


<210> SEQ ID NO 7
<211> LENGTH: 342
<212> TYPE: DNA
<213> ORGANISM: Artificial
<220> FEATURE:
<223> OTHER INFORMATION: synthetic mutant
<220> FEATURE:
<221> NAME/KEY: CDS
<222> LOCATION: (1)..(339)

<400> SEQUENCE: 7

gaa gat aaa aaa cat gat tat caa aat gaa ttt gat ttc tta ttg atg       48
```

-continued

```
Glu Asp Lys Lys His Asp Tyr Gln Asn Glu Phe Asp Phe Leu Leu Met
1               5                   10                  15

gaa cgt att cat gaa caa att aaa aaa ggt gaa ctt gca ttg ttc tat        96
Glu Arg Ile His Glu Gln Ile Lys Lys Gly Glu Leu Ala Leu Phe Tyr
            20                  25                  30

ctt caa gaa cag att aat cat ttt gaa gaa aaa ccg aca aaa gaa atg       144
Leu Gln Glu Gln Ile Asn His Phe Glu Glu Lys Pro Thr Lys Glu Met
        35                  40                  45

aaa gat aaa att gta gcc gaa atg gat acc att att gct atg atc gat       192
Lys Asp Lys Ile Val Ala Glu Met Asp Thr Ile Ile Ala Met Ile Asp
    50                  55                  60

ggt gta cgt ggt gta ctt gat cgt ctt atg caa cgt aaa gat tta gat       240
Gly Val Arg Gly Val Leu Asp Arg Leu Met Gln Arg Lys Asp Leu Asp
65                  70                  75                  80

att ttt gaa caa tat aat ctt gaa atg gct aaa aaa tct ggt gat att       288
Ile Phe Glu Gln Tyr Asn Leu Glu Met Ala Lys Lys Ser Gly Asp Ile
                85                  90                  95

ttg gaa gct gat ttg aaa gca gaa gaa gca cgt gtt aaa aag att gaa       336
Leu Glu Ala Asp Leu Lys Ala Glu Glu Ala Arg Val Lys Lys Ile Glu
            100                 105                 110

gtt taa                                                               342
Val


<210> SEQ ID NO 8
<211> LENGTH: 113
<212> TYPE: PRT
<213> ORGANISM: Artificial
<220> FEATURE:
<223> OTHER INFORMATION: synthetic mutant

<400> SEQUENCE: 8

Glu Asp Lys Lys His Asp Tyr Gln Asn Glu Phe Asp Phe Leu Leu Met
1               5                   10                  15

Glu Arg Ile His Glu Gln Ile Lys Lys Gly Glu Leu Ala Leu Phe Tyr
            20                  25                  30

Leu Gln Glu Gln Ile Asn His Phe Glu Glu Lys Pro Thr Lys Glu Met
        35                  40                  45

Lys Asp Lys Ile Val Ala Glu Met Asp Thr Ile Ile Ala Met Ile Asp
    50                  55                  60

Gly Val Arg Gly Val Leu Asp Arg Leu Met Gln Arg Lys Asp Leu Asp
65                  70                  75                  80

Ile Phe Glu Gln Tyr Asn Leu Glu Met Ala Lys Lys Ser Gly Asp Ile
                85                  90                  95

Leu Glu Ala Asp Leu Lys Ala Glu Glu Ala Arg Val Lys Lys Ile Glu
            100                 105                 110

Val


<210> SEQ ID NO 9
<211> LENGTH: 34
<212> TYPE: DNA
<213> ORGANISM: Artificial
<220> FEATURE:
<223> OTHER INFORMATION: synthetic primer

<400> SEQUENCE: 9

cattttgaag aaaaagcgac aaaagaaatg aaag                                  34


<210> SEQ ID NO 10
<211> LENGTH: 34
<212> TYPE: DNA
```

-continued

```
<213> ORGANISM: Artificial
<220> FEATURE:
<223> OTHER INFORMATION: synthetic primer

<400> SEQUENCE: 10

ctttcatttc ttttgtcgct ttttcttcaa aatg                            34


<210> SEQ ID NO 11
<211> LENGTH: 31
<212> TYPE: DNA
<213> ORGANISM: Artificial
<220> FEATURE:
<223> OTHER INFORMATION: synthetic primer

<400> SEQUENCE: 11

gatcgtctta tgcaacgtgc agatttagat a                               31


<210> SEQ ID NO 12
<211> LENGTH: 30
<212> TYPE: DNA
<213> ORGANISM: Artificial
<220> FEATURE:
<223> OTHER INFORMATION: synthetic primer

<400> SEQUENCE: 12

tatctaaatc tgcacgttgc ataagacgat                                 30


<210> SEQ ID NO 13
<211> LENGTH: 39
<212> TYPE: DNA
<213> ORGANISM: Artificial
<220> FEATURE:
<223> OTHER INFORMATION: synthetic primer

<400> SEQUENCE: 13

catcacggat ccgaagctaa aaaacatgat tatgcgaat                       39


<210> SEQ ID NO 14
<211> LENGTH: 62
<212> TYPE: DNA
<213> ORGANISM: Artificial
<220> FEATURE:
<223> OTHER INFORMATION: synthetic primer

<400> SEQUENCE: 14

cgcgcaagct tttaaacttc aatcttttta acacgtgctt cttctgcttt caaatcagct  60

tc                                                               62
```